United States Patent
Ogasawara

(10) Patent No.: US 8,094,929 B2
(45) Date of Patent: Jan. 10, 2012

(54) COLOR IDENTIFYING APPARATUS AND COLOR IDENTIFYING METHOD

(75) Inventor: Toshihiro Ogasawara, Tokyo (JP)

(73) Assignee: NEC Corporation, Tokyo (JP)

( * ) Notice: Subject to any disclaimer, the term of this patent is extended or adjusted under 35 U.S.C. 154(b) by 1021 days.

(21) Appl. No.: 12/010,550

(22) Filed: Jan. 25, 2008

(65) Prior Publication Data

US 2008/0267493 A1 Oct. 30, 2008

(30) Foreign Application Priority Data

Jan. 26, 2007 (JP) ................................ 2007-016644

(51) Int. Cl.
*G06K 9/00* (2006.01)
*G06K 9/62* (2006.01)
*G06K 9/64* (2006.01)
*G06K 9/68* (2006.01)
*G01J 3/46* (2006.01)
*G01J 1/48* (2006.01)
*G01N 21/00* (2006.01)
*G01N 21/75* (2006.01)

(52) U.S. Cl. ........ 382/162; 382/100; 382/209; 382/217; 382/218; 356/402; 422/86; 436/164

(58) Field of Classification Search .................. 382/162, 382/209, 217, 218, 100; 436/164; 422/86; 356/402
See application file for complete search history.

(56) References Cited

U.S. PATENT DOCUMENTS

| 6,228,657 B1 | 5/2001 | Genovese et al. |
| 6,320,578 B1 | 11/2001 | Shiitani et al. |
| 7,746,474 B2 * | 6/2010 | Oda ................................ 356/402 |
| 2002/0081026 A1 * | 6/2002 | Izume et al. ................... 382/170 |
| 2005/0123180 A1 * | 6/2005 | Luo et al. ...................... 382/128 |
| 2006/0008919 A1 * | 1/2006 | Boay et al. .................... 436/164 |
| 2007/0009388 A1 | 1/2007 | Oda |
| 2007/0070365 A1 * | 3/2007 | Boregowda et al. ........... 358/1.9 |

FOREIGN PATENT DOCUMENTS

| JP | 11-345319 (A) | 12/1999 |
| JP | 2006-47305 (A) | 2/2006 |

OTHER PUBLICATIONS

Japanese Office Action dated Aug. 31, 2011, with partial English translation.

* cited by examiner

*Primary Examiner* — Bernard Krasnic
(74) *Attorney, Agent, or Firm* — McGinn IP Law Group PLLC

(57) ABSTRACT

A color identifying apparatus for identifying the color of a reaction surface which has caused a color reaction with a gas to be specified, includes a reference data storage that stores a plurality of associated sets of reference color information represented by the difference between one and the remaining other two of signal intensities of R, G, B signals of RGB bitmap images of a reaction surface which has caused a color reaction with a gas, and identifying information for identifying the reaction surface, an image capturing unit for capturing an image of the reaction surface and generating RGB bitmap images of the reaction surface, an arithmetic unit for generating color information represented by the difference between one and the remaining other two signal intensities of R, G, B signals from the RGB bitmap images generated by the image capturing unit, and an output unit for outputting the identifying information.

6 Claims, 11 Drawing Sheets

(a)

(b)

| CATEGORY | COORDINATES | | SIGNAL INTENSITY | | | GRADIENT | |
|---|---|---|---|---|---|---|---|
| | x | y | R | G | B | Arg(1) | Agb(1) |
| | 0 | 0 | 51 | 101 | 202 | | |
| | 0 | 1 | 50 | 99 | 199 | | |
| | 0 | 2 | 52 | 95 | 200 | | |
| | ... | | | | | | |
| | 300 | 240 | 48 | 105 | 205 | | |
| | 300 | 241 | 51 | 103 | 202 | | |
| | 300 | 242 | 50 | 99 | 199 | | |
| | 300 | 243 | 52 | 95 | 200 | | |
| | 300 | 244 | 49 | 99 | 201 | | |
| REFERENCE DATA | 300 | 245 | 51 | 101 | 198 | | |
| D(i) | 300 | 246 | 47 | 102 | 196 | | |
| i=1 | ... | | | | | | |
| | 50 | 479 | 51 | 101 | 198 | | |
| | 51 | 80 | 52 | 95 | 200 | | |
| | 51 | 81 | 51 | 103 | 202 | | |
| | 51 | 82 | 49 | 99 | 201 | | |
| | 51 | 83 | 48 | 102 | 205 | | |
| | 51 | 84 | 50 | 99 | 195 | | |
| | 51 | 85 | 47 | 102 | 197 | | |
| | ... | | | | | | |
| | 639 | 477 | 51 | 103 | 202 | | |
| | 639 | 478 | 49 | 99 | 201 | | |
| | 639 | 479 | 48 | 105 | 205 | | |
| | AVERAGE VALUE | | 50 | 100 | 200 | 51 | 100 |

| CATEGORY | COORDINATES | | SIGNAL INTENSITY | | | GRADIENT | |
|---|---|---|---|---|---|---|---|
| | x | y | R | G | B | Δrg(2) | Δgb(2) |
| REFERENCE DATA D(i) i=2 | 0 | 0 | 49 | 99 | 121 | | |
| | 0 | 1 | 51 | 101 | 118 | | |
| | 0 | 2 | 47 | 102 | 123 | | |
| | ... | | | | | | |
| | 300 | 240 | 48 | 102 | 115 | | |
| | 300 | 241 | 50 | 99 | 125 | | |
| | 300 | 242 | 47 | 102 | 124 | | |
| | 300 | 243 | 49 | 99 | 119 | | |
| | 300 | 244 | 48 | 105 | 115 | | |
| | 300 | 245 | 48 | 102 | 120 | | |
| | 300 | 246 | 50 | 99 | 118 | | |
| | ... | | | | | | |
| | 50 | 479 | 51 | 101 | 119 | | |
| | 51 | 80 | 52 | 95 | 115 | | |
| | 51 | 81 | 51 | 103 | 116 | | |
| | 51 | 82 | 49 | 99 | 125 | | |
| | 51 | 83 | 48 | 102 | 121 | | |
| | 51 | 84 | 50 | 99 | 118 | | |
| | 51 | 85 | 47 | 102 | 120 | | |
| | ... | | | | | | |
| | 639 | 477 | 51 | 101 | 118 | | |
| | 639 | 478 | 47 | 102 | 115 | | |
| | 639 | 479 | 50 | 99 | 129 | | |
| AVERAGE VALUE | | | 49 | 101 | 120 | 52 | 19 |

FIG.6

| CATEGORY | COORDINATES | | SIGNAL INTENSITY | | | GRADIENT | |
|---|---|---|---|---|---|---|---|
| | x | y | R | G | B | $\Delta rg(3)$ | $\Delta gb(3)$ |
| REFERENCE DATA D(I) I=3 | 0 | 0 | 39 | 89 | 111 | | |
| | 0 | 1 | 41 | 91 | 108 | | |
| | 0 | 2 | 37 | 92 | 113 | | |
| | ... | | | | | | |
| | 300 | 240 | 38 | 92 | 105 | | |
| | 300 | 241 | 40 | 89 | 115 | | |
| | 300 | 242 | 37 | 92 | 114 | | |
| | 300 | 243 | 39 | 88 | 109 | | |
| | 300 | 244 | 38 | 95 | 105 | | |
| | 300 | 245 | 38 | 92 | 110 | | |
| | 300 | 246 | 40 | 89 | 108 | | |
| | ... | | | | | | |
| | 50 | 479 | 41 | 91 | 109 | | |
| | 51 | 80 | 42 | 85 | 105 | | |
| | 51 | 81 | 41 | 93 | 105 | | |
| | 51 | 82 | 39 | 88 | 115 | | |
| | 51 | 83 | 38 | 92 | 111 | | |
| | 51 | 84 | 40 | 89 | 109 | | |
| | 51 | 85 | 37 | 92 | 110 | | |
| | ... | | | | | | |
| | 639 | 477 | 41 | 91 | 108 | | |
| | 639 | 478 | 37 | 92 | 105 | | |
| | 639 | 479 | 40 | 89 | 119 | | |
| AVERAGE VALUE | | | 39 | 91 | 110 | 52 | 19 |

FIG. 7

| CATEGORY | COORDINATES | | SIGNAL INTENSITY | | | GRADIENT | |
|---|---|---|---|---|---|---|---|
| | x | y | R | G | B | Δrg(r) | Δrb(r) |
| MEASURED DATA D(r) | 300 | 0 | 50 | 99 | 119 | | |
| | 300 | 1 | 55 | 102 | 120 | | |
| | 300 | 2 | 47 | 102 | 124 | | |
| | ... | | | | | | |
| | 300 | 240 | 51 | 108 | 118 | | |
| | 300 | 241 | 56 | 102 | 115 | | |
| | 300 | 242 | 49 | 99 | 125 | | |
| | 300 | 243 | 52 | 102 | 118 | | |
| | 300 | 244 | 48 | 105 | 115 | | |
| | 300 | 245 | 50 | 99 | 125 | | |
| | 300 | 246 | 50 | 89 | 118 | | |
| | ... | | | | | | |
| | 50 | 478 | 51 | 101 | 119 | | |
| | 51 | 80 | 52 | 85 | 115 | | |
| | 51 | 81 | 51 | 103 | 115 | | |
| | 51 | 82 | 49 | 105 | 125 | | |
| | 51 | 83 | 55 | 102 | 115 | | |
| | 51 | 84 | 50 | 85 | 119 | | |
| | 51 | 85 | 47 | 102 | 120 | | |
| | ... | | | | | | |
| | 638 | 477 | 51 | 105 | 118 | | |
| | 639 | 478 | 47 | 106 | 115 | | |
| | 639 | 478 | 55 | 99 | 121 | | |
| AVERAGE VALUE | | | 51 | 102 | 119 | 51 | 17 |

Fig. 10

$$ERR(i) = \sqrt{(\Delta rg(r) - \Delta rg(i))^2 + (\Delta gb(r) - \Delta gb(i))^2}$$

Fig. 11

| MEASURED DATA D(r) | | REFERENCE DATA D(1) | | | REFERENCE DATA D(2) | | |
|---|---|---|---|---|---|---|---|
| Δrg(r) | Δgb(r) | Δrg(1) | Δgb(1) | ERROR (1) | Δrg(2) | Δgb(2) | ERROR (2) |
| 51 | 17 | 51 | 100 | 83 | 52 | 19 | 2 | ary object of the invention is to provide a color identifying device and a color identifying method which are capable of identifying the color of a reaction surface with a relatively small amount of data.
COLOR IDENTIFYING APPARATUS AND COLOR IDENTIFYING METHOD

CROSS REFERENCE TO RELATED APPLICATIONS

This application is based upon and claims the benefit of priority from Japanese patent application No. 2007-16644, filed on Jan. 26, 2007, the disclosure of which is incorporated herein in its entirety by reference.

BACKGROUND OF THE INVENTION

1. Field of the Invention

The present invention relates to a color identifying apparatus and a color identifying method, and more particularly to a color identifying apparatus and a color identifying method for specifying a gas by identifying the color of a reaction surface which is produced by a color reaction with the gas.

2. Description of the Related Art

There have heretofore been known gas detecting devices for causing a chemical reaction between a gas such as a toxic gas and chemical reagents to change the colors of the chemical reagents. For example, U.S. Pat. No. 6,228,657B1 discloses an M256 chemical agent detection kit.

The gas detecting device includes a plurality of ampules containing respective chemical reagents of different types and a plurality of reaction surfaces such as paper surfaces. When the ampules are crushed, the chemical reagents contained therein flow into the reaction surfaces.

The chemical reagents as they flow into the reaction surfaces chemically react with a gas that is held in contact with the reaction surfaces. The chemical reaction causes the chemical reagents to change their colors, and the reaction surfaces also change their colors depending on the color changes of the chemical reagents.

The user of the gas detecting device introduces different chemical reagents into the respective reaction surfaces, and recognizes the concentration of the gas based on the color changes of the reaction surfaces.

U.S. Pat. No. 6,228,657B1 also reveals a reader device for outputting a signal depending on the color of a reaction surface using three photodiodes or a single color CCD sensitive to the colors of R, G, B (red, green, and blue).

The brightness of the color of a reaction surface, which is caused by a color reaction with a gas, varies depending on the concentration of the gas. Therefore, the brightness of the reaction surface varies if the concentration of the gas varies even though the components of the gas remain the same.

Consequently, if the color of an actual reaction surface is specified by checking the data of the color read from the actual reaction surface against the pre-registered data of the colors of reaction surfaces, then since it is necessary to pre-register the data of colors produced by color reactions with a gas at different concentrations, the amount of data required to be pre-registered is very large.

SUMMARY OF THE INVENTION

An exemplary object of the invention is to provide a color identifying device and a color identifying method which are capable of identifying the color of a reaction surface with a relatively small amount of data.

A color identifying apparatus according to an exemplary aspect of the invention is a color identifying apparatus for identifying a color of a reaction surface which has caused a color reaction with a gas to be specified, the color identifying apparatus includes: a reference data storage that stores a plurality of associated sets of reference color information represented by the difference between one and the remaining other two of signal intensities of R, G, B signals of RGB bitmap images of a reaction surface which has caused a color reaction with a gas, and identifying information for identifying the reaction surface; an image capturing unit that captures an image of the reaction surface and generates RGB bitmap images of the reaction surface; an arithmetic unit that generates color information represented by the difference between one and the remaining other two signal intensities of R, G, B signals from the RGB bitmap images generated by the image capturing unit, checks the generated color information against the reference color information stored in the reference data storage, specifies the reference color information which corresponds to the generated color information, and specifies the identifying information which is related to the specified reference color information; and an output unit that outputs the identifying information specified by the arithmetic unit.

A color identifying method according to an exemplary aspect of the invention is a color identifying method adapted to be carried out by a color identifying apparatus including a reference data storage, the color identifying method includes: storing, in the reference data storage, a plurality of associated sets of reference color information represented by the difference between one and the remaining other two of signal intensities of R, G, B signals of RGB bitmap images of a reaction surface which has caused a color reaction with a gas, and identifying information for identifying the reaction surface; capturing an image of the reaction surface and generating RGB bitmap images of the reaction surface; generating color information represented by the difference between one and the remaining other two signal intensities of R, G, B signals from the generated RGB bitmap images; specifying the reference color information which corresponds to the generated color information by checking the generated color information against the reference color information stored in the reference data storage; specifying the identifying information which is related to the specified reference color information; and outputting the specified identifying information.

The above and other objects, features, and advantages of the present invention will become apparent from the following description with reference to the accompanying drawings which illustrate an example of the present invention.

BRIEF DESCRIPTION OF THE DRAWINGS

FIG. 4 is a diagram showing the details of reference data D(1);

FIG. 5 is a diagram showing the details of reference data D(2);

FIG. 6 is a diagram showing the details of reference data D(3);

FIG. 7 is a diagram showing the details of measured data D(r);

FIG. 10 is a diagram showing an equation for calculating error ERR; and

FIG. 11 is a diagram showing an example of calculated results of error ERR.

DETAILED DESCRIPTION OF THE PREFERRED EMBODIMENT

A color identifying device and a color identifying method according to an exemplary embodiment of the present invention will be described below with reference to the accompanying drawings.

Figure 1:
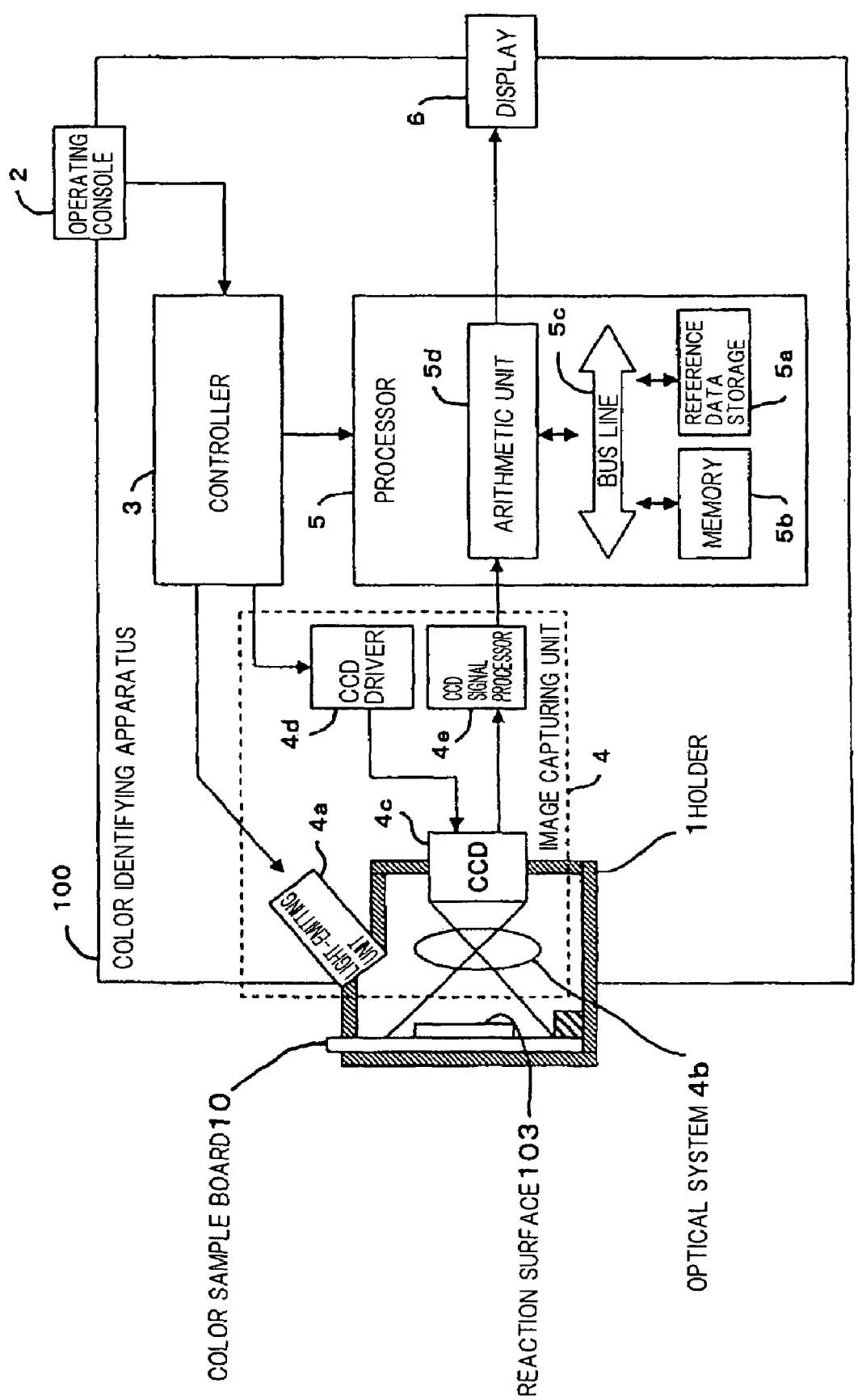
FIG. 1 is a block diagram of a color identifying device according to an exemplary embodiment of the present invention.

FIG. 1 shows in block form color identifying device 100 according to an exemplary embodiment of the present invention.

As shown in FIG. 1, color identifying device 100 comprises holder 1, operating console 2, controller 3, image capturing unit 4, processor 5 and display 6. Image capturing unit 4 includes light-emitting unit 4a, optical system 4b, CCD 4c, CCD driver 4d and CCD signal processor 4e. Processor 5 includes reference data storage 5a, memory 5b, bus line 5c and arithmetic unit 5d.

Color sample board 10 is mounted in a predetermined position in holder 1.

Color sample board 10 has reaction surface 103 disposed in a predetermined position thereon.

Figure 2:
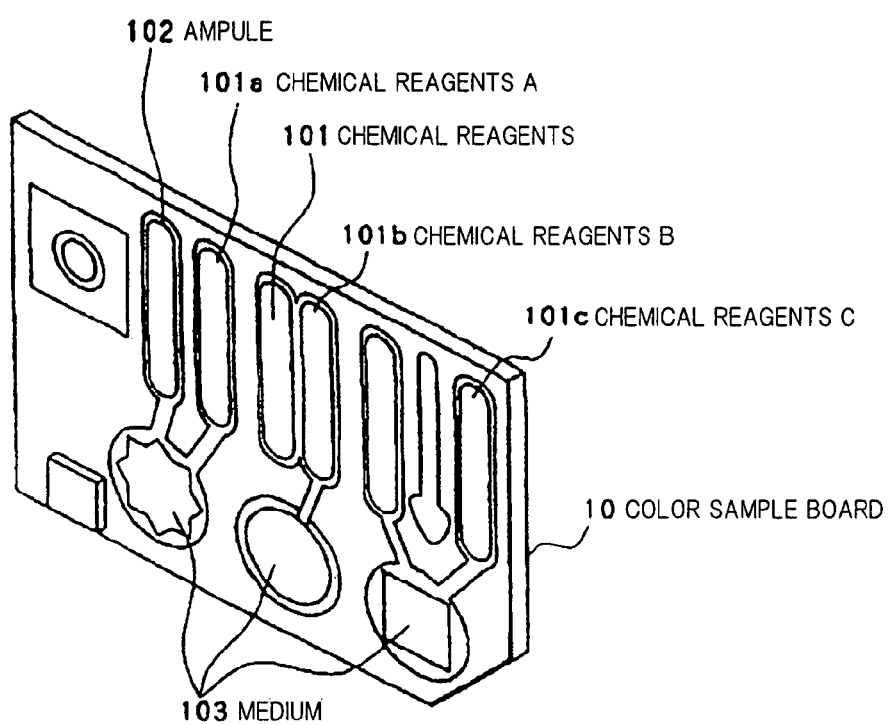
FIG. 2 is a perspective view of color sample board 10.

FIG. 2 shows a perspective color sample board 10 by way of example.

As shown in FIG. 2, color sample board 10 has a plurality of chemical reagents 101, a plurality of ampules 102 and a plurality of mediums 103. Ampules 102 contain chemical reagents 101 (e.g., 101a, 101b, 101c), respectively, which are of different types. Mediums 103 are in the form of respective sheets of paper or the like. When ampules 102 are crushed, chemical reagents contained therein flow into mediums 103. Mediums 103 provide reaction surfaces 103, respectively.

When each chemical reagent 101 flows into medium 103, each chemical reagent 101 causes a color reaction with a gas, e.g., a gas to be identified, which is held in contact with medium 103. The M256 chemical agent detection kit disclosed in U.S. Pat. No. 6,228,657B1, for example, may be used as color sample board 10.

In FIG. 1, color identifying device 100 identifies the gas based on the colors of reaction surface 103 which has caused the color reaction.

Operating console 2 has an operation start button (not shown) which can be operated by the user. When the operation start button is operated, operating console 2 supplies a light emission instruction to controller 3.

In response to the light emission instruction from operating console 2, controller 3 controls the operation of image capturing unit 4 and processor 5. Specifically, in response to the light emission instruction from operating console 2, controller 3 controls light-emitting unit 4a to emit light, supplies a drive signal to CCD driver 4d, and operates processor 5.

Image capturing unit 4 can generally be called an image capturing means.

In response to an instruction from controller 3, image capturing unit 4 captures an image of reaction surface 103 of color sample board 10 that is mounted in holder 1, and generates RGB bitmap images (hereinafter referred to as "RGB bitmap data") of reaction surface 103. Of the RGB, R stands for red, G for green, and B for blue.

Light-emitting unit 4a is controlled by controller 3 to apply light to reaction surface 103 of color sample board 10 mounted in holder 1. Light-emitting unit 4a comprises a halogen lamp or an LED, for example. However, light-emitting unit 4a is not limited to a halogen lamp or an LED, but may comprise another light source.

Reaction surface 103 reflects the light emitted from light-emitting unit 4a. When reaction surface 103 causes a color reaction with a gas to be identified, the light reflected by reaction surface 103 represents a color that is generated by the color reaction.

Holder 1 prevents light, which is different from the applied light from light-emitting unit 4a, from being applied to color sample board 10.

Optical system 4b comprises a lens, for example, and produces an image of reaction surface 103 of color sample board 10 mounted in holder 1 onto CCD 4c.

CCD 4c is an example of a color image capturing device. The color image capturing device is not limited to a CCD, but may be any of other image capturing devices, e.g., a CMOS sensor.

In response to the drive signal from controller 3, CCD driver 4d operates CCD 4c to capture a color image of reaction surface 103 which is formed on CCD 4c. CCD 4c supplies an analog color image signal representing the captured color image of reaction surface 103 to CCD signal processor 4e.

CCD signal processor 4e converts the analog color image signal from CCD 4c into a digital signal (RGB bitmap data), and supplies the RGB bitmap data to processor 5.

According to the RGB bitmap data, each bit (pixel) is represented by R, G, B signals each having a signal intensity in a range from 0 to 255. The signal intensity range of each of the R, G, B signals is not limited to 0 to 255, but may be another range.

Processor 5 processes the RGB bitmap data from CCD signal processor 4e to identify the color of reaction surface 103, and outputs information depending on the identified color.

Reference data storage 5a can generally be called reference data storage means.

Reference data storage 5a stores a plurality of associated sets of reference color information, which is represented by the difference between one and the remaining other two signal intensities of the R, G, B signals of RGB bitmap images of a reaction surface which has caused a color reaction with a gas, and identifying information for identifying the reaction surface.

Memory 5b is used as a working memory of arithmetic unit 5d.

Arithmetic unit 5d can generally be called arithmetic means.

Arithmetic unit 5d operates by executing a program, for example.

Arithmetic unit 5d is connected to reference data storage 5a and memory 5b by bus line 5c.

Arithmetic unit 5d generates color information represented by the difference between one signal intensity and the other two signal intensities of the R, G, B signals from the RGB bitmap image data generated by image capturing unit 4.

For example, arithmetic unit 5d calculates average values of the signal intensities of the respective R, G, B signals for all the pixels from the RGB bitmap image data generated by image capturing unit 4, and generates color information represented by the differences between one and the other two of the average values of the signal intensities of the respective R, G, B signals.

Arithmetic unit 5d checks the generated color information against the plural items of reference color information stored in reference data storage 5a, and identifies the reference color information corresponding to the generated color information. For example, arithmetic unit 5d identifies the reference color information which is the most similar to the generated color information.

Arithmetic unit 5d specifies the identifying information that is related to the reference color information which has been identified, and outputs the specified identifying information to display 6.

Display 6 can generally be called output means.

Display 6 is an example of an output unit and displays the identifying information specified by arithmetic unit 5d. The output unit is not limited to the display, but may be another output unit such as a speech output unit for outputting a speech signal representing the specified identifying information.

The reference color information stored in reference data storage 5a should preferably be color information which is generated by arithmetic unit 5d from RGB bitmap data that are produced when image capturing unit 4 captures images of reaction surfaces which caused color reactions with gases.

However, the reference color information stored in reference data storage 5a is not limited to color information generated by arithmetic unit 5d.

The principles of a color identification process carried out by arithmetic unit 5d will be described below.

Figure 3A:
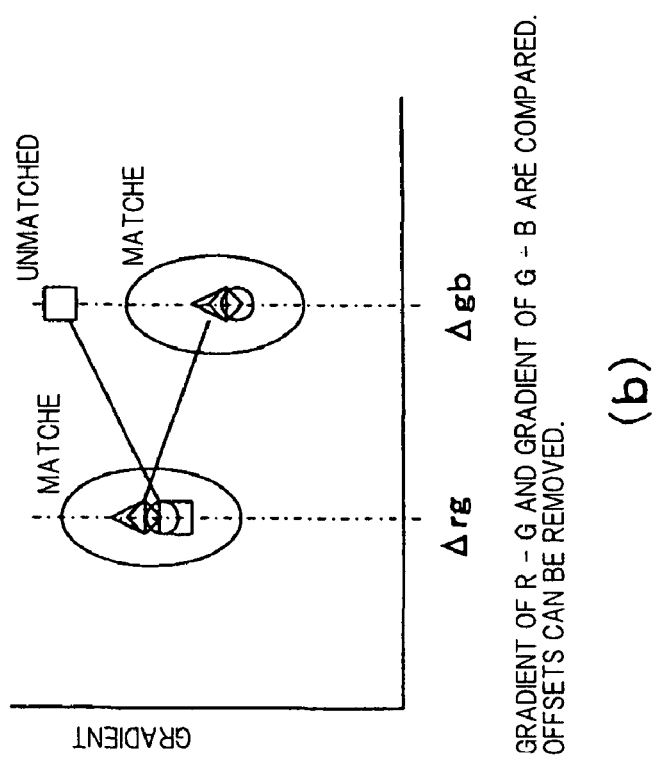
FIG. 3A is a diagram illustrative of the principles of a color identification process that is carried out by arithmetic unit 5d.
Figure 3B:
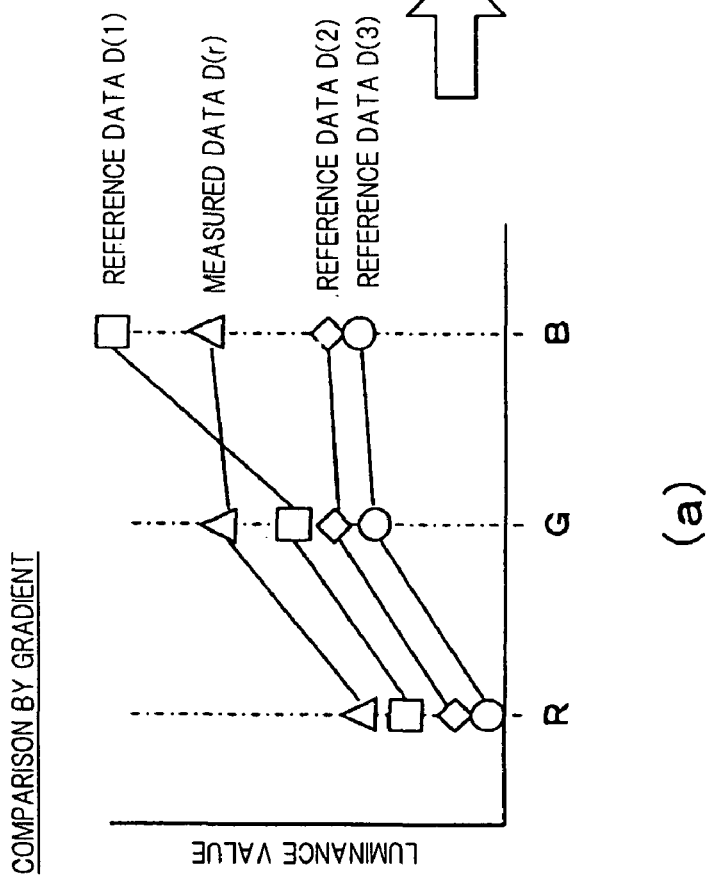
FIG. 3B is a diagram illustrative of the principles of the color identification process that is carried out by arithmetic unit 5d.

FIG. 3A is a graph showing R, G, B signal intensities (luminance values) obtained from RGB bitmap data.

Specifically, FIG. 3A shows R, G, B luminance values of three reference data D1(1) through D(3) obtained respectively from three RGB bitmap data, and R, G, B luminance values of measured data D(r) obtained from one RGB bitmap data.

The color represented by reference data D(1) and the color represented by reference data D(2) have different hues, and the color represented by reference data D(2) and the color represented by reference data D(3) have the same hue, but different brightness values.

A review of reference data D(2) and reference data D(3) shown in FIG. 3A indicates that the R, G, B signal intensities of the RGB bitmap data, which have the same hue, but different brightness values, have different offsets depending on the different brightness values.

When the differences between one signal intensity and the other two of the R, G, B signal intensities (e.g., G-R and B-G) are calculated, the different offsets depending on the different brightness values are canceled out. Therefore, the color information remains unchanged when the brightness changes, and the color information changes when the hue changes.

When a chemical reagent on a reaction surface causes a color reaction with gases, the hue produced by the color reaction remains the same if the gases are identical, but the brightness produced by the color reaction changes if the gases are identical but have different concentrations. Therefore, the color information is independent of gas concentration differences, but changes depending on the type of the gas involved.

According to the classification based on the color information, reference data D(1) and reference data D(2) are classified into different categories, and reference data D(2) and reference data D(3) are classified into the same category.

FIG. 4 is a diagram showing the details of reference data D(1). FIG. 5 is a diagram showing the details of reference data D(2). FIG. 6 is a diagram showing the details of reference data D(3). FIG. 7 is a diagram showing the details of measured data D(r).

Figure 8:
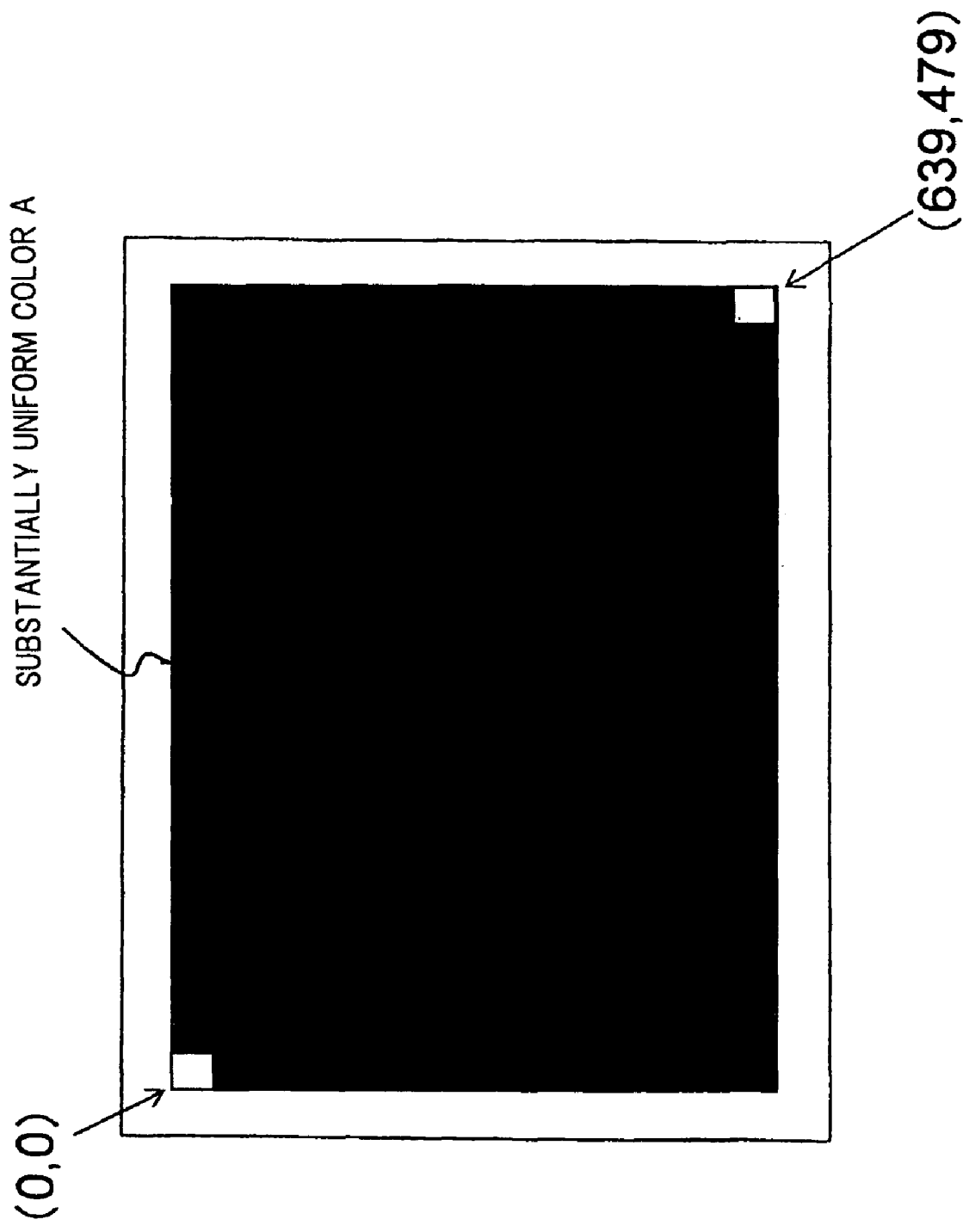
FIG. 8 is a diagram illustrative of the coordinate values of pixels of RGB bitmap data.

Reference data D(1) shown in FIG. 4 include R; G, B signal intensities at coordinates (x, y) (see FIG. 8) of the pixels of the RGB bitmap data, average values of the R, G, B signal intensities of all the pixels, and color information $\Delta rg(1)$ and $\Delta gb(1)$.

Color information $\Delta rg(1)$ is expressed by (the average value of the G signal intensities)−(the average value of the R signal intensities), and color information $\Delta gb(1)$ is expressed by (the average value of the B signal intensities)−(the average value of the G signal intensities). The coordinates of the pixels are not limited to the illustrated coordinates, but may be changed.

Reference data D(2) shown in FIG. 5 include R, G, B signal intensities at coordinates (x, y) of the pixels of the RGB bitmap data, average values of the R, G, B signal intensities of all the pixels, and color information $\Delta rg(2)$ and $\Delta gb(2)$.

Color information $\Delta rg(2)$ is expressed by (the average value of the G signal intensities)−(the average value of the R signal intensities), and color information $\Delta gb(2)$ is expressed by (the average value of the B signal intensities)−(the average value of the G signal intensities). The coordinates of the pixels are not limited to the illustrated coordinates, but may be changed.

Reference data D(3) shown in FIG. 6 include R, G, B signal intensities at coordinates (x, y) of the pixels of the RGB bitmap data, average values of the R, G, B signal intensities of all the pixels, and color information $\Delta rg(3)$ and $\Delta gb(3)$.

Color information $\Delta rg(3)$ is expressed by (the average value of the G signal intensities)−(the average value of the R signal intensities), and color information $\Delta gb(3)$ is expressed by (the average value of the B signal intensities)−(the average value of the G signal intensities). The coordinates of the pixels are not limited to the illustrated coordinates, but may be changed.

Measured data D(r) shown in FIG. 7 include R, G, B signal intensities at coordinates (x, y) of the pixels of the RGB bitmap data, average values of the R, G, B signal intensities of all the pixels, and color information $\Delta rg(r)$, $\Delta gb(r)$.

Color information $\Delta rg(r)$ is expressed by (the average value of the G signal intensities)−(the average value of the R signal intensities), and color information $\Delta gb(r)$ is expressed by (the average value of the B signal intensities)−(the average value of the G signal intensities). The coordinates of the pixels are not limited to the illustrated coordinates, but may be changed.

The color information ($\Delta rg$, $\Delta gb$) represents the differences between one (G) signal intensity and the other two (R, B) signal intensities of the R, G, B signal intensities. The color information is not limited to the difference between the R and G signal intensities and the difference between the G and B signal intensities, but may be a set of the difference between the G and B signal intensities and the difference between the B and R signal intensities, or a set of the difference between the B and R signal intensities and the difference between the R and G signal intensities.

Arithmetic unit 5d can identify the color represented by measure data D(r) by determining the reference data having color information which best matches the color information of reference data D(r).

The color information ($\Delta rg$, $\Delta gb$) remains the same if the hue is the same, but the brightness differs. Therefore, the reference color information stored in reference data storage 5a does not need to be dependent on different gas concentrations. It is thus possible to identify the color of a reaction surface with a relatively small amount of data.

Operation of color identifying device 100 according to the present exemplary embodiment will be described below.

Color identifying device 100 stores reference data and identifying information thereof in reference data storage 5a. Thereafter, color identifying device 100 identifies the color of reaction surface 103 based on RGB bitmap data of reaction surface 103 which are generated by image capturing unit 4 and the reference color information stored in reference data storage 5a, and outputs information representing the identified color.

Figure 9:
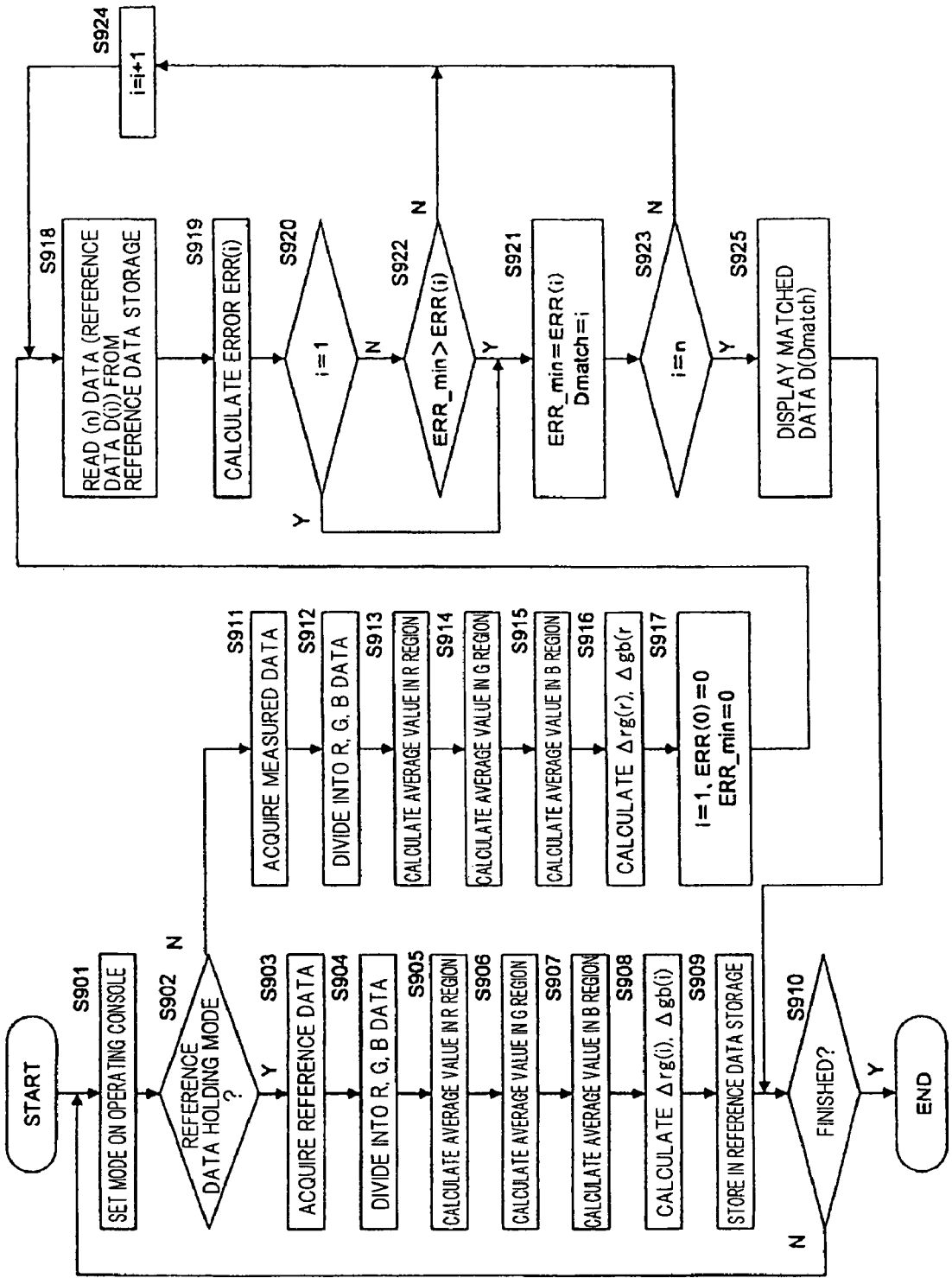
FIG. 9 is a flowchart of an operation sequence of color identifying device 100.

FIG. 9 is an operation sequence of color identifying device 100.

First, an operation sequence of color identifying device 100 for storing data in reference data storage 5a will be described below.

The user inserts color sample board 10 having reaction surface 103 which has caused a color reaction with a specified gas into a given position in holder 1.

The user then operates a reference data holding button (not shown) on operating console 2, placing color identifying device 100 into a reference data holding mode in step 901.

When the user operates an operation start button (not shown) on operating console 2 while in the reference data holding mode in step 902, operating console 2 supplies a light emission instruction to controller 3.

In response to the light emission instruction from operating console 2, controller 3 controls light-emitting unit 4a to emit light, supplies a drive signal to CCD driver 4d, and operates processor 5.

Reaction surface 103 reflects the light emitted from light-emitting unit 4a, and optical system 4b focuses an image of reaction surface 103 onto CCD 4c. Based on a drive signal from controller 3, CCD driver 4d energizes CCD 4c to capture the image of reaction surface 103 on CCD 4c.

CCD 4c supplies an analog color image signal representing the captured image of reaction surface 103 to CCD signal processor 4e. CCD signal processor 4e converts the analog color image signal into RGB bitmap data, and supplies the RGB bitmap data to arithmetic unit 5d.

Arithmetic unit 5d acquires the RGB bitmap data (reference data) in step 903.

Then, arithmetic unit 5d divides the RGB bitmap data into signal intensity data in respective R, G, B regions, and sends the signal intensity data in the respective R, G, B regions through bus line 5c to memory 5b where they are stored in step 904.

Then, arithmetic unit 5d determines signal intensities in the R region of the respective pixels, and calculates an average value of the signal intensities in the R region in step 905.

Then, arithmetic unit 5d determines signal intensities in the G region of the respective pixels, and calculates an average value of the signal intensities in the G region in step 906.

Then, arithmetic unit 5d determines signal intensities in the B region of the respective pixels, and calculates an average value of the signal intensities in the B region in step 907.

Then, arithmetic unit 5d calculates reference color information ($\Delta rg(i)$, $\Delta gb(i)$). Specifically, arithmetic unit 5d subtracts the average value of the signal intensities in the R region calculated in step 905 from the average value of the signal intensities in the G region calculated in step 906 to calculate reference color information $\Delta rg(i)$, and subtracts the average value of the signal intensities in the G region calculated in step 906 from the average value of the signal intensities in the B region calculated in step 907 to calculate reference color information $\Delta gb(i)$ in step 908.

Then, arithmetic unit 5d displays a message for prompting the user to enter a category (identifying information) such as a data name or the like, on display 6. When the user operates operating console 2 based on the message to enter a category, operating console 2 supplies the entered category to controller 3, which supplies the category to arithmetic unit 5d.

The category will be used as a data name when finally identified data are displayed on display 6.

When arithmetic unit 5d receives the category, arithmetic unit 5d associates the category with the R, G, B signal intensities and reference color information ($\Delta rg(i)$, $\Delta gb(i)$) calculated in step 908, and stores all the data as a lump in reference data storage 5a through bus line 5c in step 909. The data stored in reference data storage 5a have a structure as shown in FIG. 4.

Thereafter, the above process is repeated as the user changes color sample board 10 in holder 1 to successive color sample boards 10 whose reaction surfaces 103 have chemically reacted with gases of different gas components in step 910.

Then, arithmetic unit 5d identifies the color of reaction surface 103 based on the RGB bitmap data of reaction surface 103 which are generated by image capturing unit 4 and the reference color information stored in reference data storage 5a, and outputs information representing the identified color. Such a process of arithmetic unit 5d will be described below with reference to FIG. 9.

The user inserts color sample board 10 having reaction surface 103 which has caused a color reaction with a gas to be specified into a given position in holder 1.

The user then operates the reference data holding button (not shown) on operating console 2, canceling the reference data holding mode in step 901.

When the user operates the operation start button on operating console 2 with the reference data holding mode being canceled in step 902, light-emitting unit 4a emits light, and CCD 4c captures an image of reaction surface 103 and supplies an analog color image signal representing the captured image of reaction surface 103 to CCD signal processor 4e. CCD signal processor 4e converts the analog color image signal into RGB bitmap data, and supplies the RGB bitmap data to arithmetic unit 5d.

Arithmetic unit 5d acquires the RGB bitmap data (measured data) in step 911.

Thereafter, arithmetic unit 5d executes steps 912 through 915. Step 912 is identical to step 904, step 913 to step 905, step 914 to step 906, and step 915 to step 907.

Then, arithmetic unit 5d calculates color information ($\Delta rg(r)$, $\Delta gb(r)$) of the measured data. Specifically, arithmetic unit 5d subtracts the average value of the signal intensities in the R region calculated in step 913 from the average value of the signal intensities in the G region calculated in step 914 to calculate color information $\Delta rg(r)$, and subtracts the average value of the signal intensities in the G region calculated in step 914 from the average value of the signal intensities in the B region calculated in step 915 to calculate color information $\Delta gb(r)$ in step 916.

Then, arithmetic unit 5d sets variable i to "1" and sets arithmetic initial values to "0" (ERR(0)=0, ERR_min=0) in step 917.

Then, arithmetic unit 5d reads reference data D(i) corresponding to variable i from reference data storage 5a, and stores read reference data D(i) in memory 5b through bus line 5c in step 918.

Then, arithmetic unit 5d refers to memory 5b, calculates an equation shown in FIG. 10 to determine error ERR(i) between the color information of the measured data and the reference color information of reference data D(i) in step 919. Error ERR(i) is smaller since the color information and the reference color information are more similar to each other.

Then, arithmetic unit 5d determines whether i=1 or not in step 920. If i=1, then arithmetic unit 5d sets ERR_min=ERR(i) and Dmatch=i in step 921.

If i is not 1, then arithmetic unit 5d determines whether ERR_min is greater than ERR(i) or not in step 922.

If ERR_min is greater than ERR(i), then arithmetic unit 5d executes step 921.

Then, arithmetic unit 5d determines whether i=n or not in step 923.

N represents the number of items of reference color information stored in reference data storage 5a.

If i is not n, then arithmetic unit 5d increments variable i by 1 in step 924, and executes step 918.

If ERR_min is not greater than ERR(i) in step 922, then arithmetic unit 5d executes step 924.

If i=n in step 923, then arithmetic unit 5d displays the category corresponding to i indicated by Dmatch as data corresponding to reaction surface 103 in holder 1 in step 925.

FIG. 11 is a diagram showing error ERR(1) between color information ($\Delta rg(r)$, $\Delta gb(r)$) of measured data D(r) shown in FIG. 7 and color information ($\Delta rg(1)$, $\Delta gb(1)$) of reference data D(i=1) shown in FIG. 4, and error ERR(2) between color information ($\Delta rg(r)$, $\Delta gb(r)$) of measured data D(r) shown in FIG. 7 and color information ($\Delta rg(2)$, $\Delta gb(2)$) of reference data D(i=2) shown in FIG. 5.

As shown in FIG. 11, since error ERR(1)=83 and error ERR(2)=2, arithmetic unit 5d judges that the color information of measured data D(r) is most similar to the reference color information of reference data D(2) and that the color information of measured data D(r) corresponds to the reference color information of reference data D(2).

According to the present exemplary embodiment, arithmetic unit 5d checks the color information generated from the RGB bitmap data from image capturing unit 4 against the plural reference color information, specifies one item of the reference color information which corresponds to the generated color information, and specifies a category that is related to the specified reference color information. This color information is represented by the differences between one signal intensity and the other two signal intensities of the RGB signal intensities.

According to the RGB bitmap data of reaction surface 103, when the brightness changes if the hue remains the same, the offsets of the R, G, B signal intensities are changed depending on the brightness.

When the differences between one signal intensity and the other two signal intensities of the R, G, B signal intensities are calculated, i.e., when the above color information is determined, the different offsets depending on the different brightness values are canceled out. Therefore, the color information remains unchanged when the brightness changes, and the color information changes when the hue changes.

When the chemical reagent on reaction surface 103 causes a color reaction with gases, the hue produced by the color reaction remains the same if the gases are identical, but the brightness produced by the color reaction changes if the gases are identical but have different concentrations. Therefore, the color information remains unchanged by gas concentration differences, but changes depending on the type of the gas involved.

The reference color information does not need to be stored in reference data storage 5a dependent on different gas concentrations. It is thus possible to identify the color of a reaction surface with a relatively small amount of data.

A color identifying apparatus, which consists of reference data storage 5a, image capturing unit 4, arithmetic unit 5d and display 6, operates in the same manner and offers the same advantages as color identifying apparatus 100 according to the present exemplary embodiment. In other words, the color identifying apparatus which consists of reference data storage 5a, image capturing unit 4, arithmetic unit 5d and display 6 is capable of identifying the color of reaction surface 103 with a relatively small amount of data.

According to the present exemplary embodiment, arithmetic unit 5d calculates errors between generated color information and a plurality of items of reference color information, specifies one item of the reference color information which has the smallest error as reference color information that is most similar to the generated color information, and specifies a category that is related to the specified reference color information.

Therefore, the colors of many reaction surfaces can be identified with a relatively small amount of data.

According to the present exemplary embodiment, arithmetic unit 5d calculates average values of R, G, B signal intensities of all the pixels from the RGB bitmap data generated by image capturing unit 4, and generates color information represented by the differences between one and other two of the average values of R, G, B signal intensities.

In this case, characteristic variations of the individual image capturing elements of CCD 4c, for example, can be averaged. Consequently, the color of reaction surface 103 can be identified with high accuracy.

According to the present exemplary embodiment, reference data storage 5a stores, in advance, color information generated by arithmetic unit 5d from the RGB bitmap data generated when image capturing unit 4 has captured images of reaction surface 103 that has caused a color reaction with gases, as reference color information.

The plural items of reference color information stored in reference data storage 5a are dependent on the characteristics of image capturing unit 4, making it easy to match the plural items of reference color information stored in reference data storage 5a and the image capturing characteristics of image capturing unit 4.

A category stored in reference data storage 5a may comprise information (e.g., gas identifying information such as a gas name) for identifying a reaction surface by a gas which has chemically reacted on the reaction surface.

It is thus possible to output identifying information for identifying a gas which has chemically reacted with reaction surface 103. Therefore, it is easy to specify the gas which has chemically reacted with the reaction surface.

According to the present exemplary embodiment, the color of a reaction surface is identified using color information generated from the RGB bitmap image of the reaction surface. The color information is represented by the differences between one and the remaining other two signal intensities of the R, G, B signal intensities.

According to the RGB bitmap image of a reaction surface, if the hue remains the same while the brightness changes, the offsets of the R, G, B signal intensities are changed depending on the brightness.

When the differences between one and the remaining other two of the R, G, B signal intensities are calculated, i.e., when the color information is determined, the different offsets depending on the different brightness values are canceled out. Therefore, the color information remains unchanged when the brightness changes, and the color information changes when the hue changes.

When the chemical reagent on a reaction surface causes a color reaction with gases, the hue produced by the color reaction remains the same if the gases are identical, but the brightness produced by the color reaction changes if the gases are identical but have different concentrations. Therefore, the color information remains unchanged by gas concentration differences, but changes depending on the type of the gas involved.

The reference color information does not need to be stored in the reference data storage for every different gas concentrations. It is thus possible to identify the color of a reaction surface with a relatively small amount of data.

The arithmetic unit should preferably calculate errors between the generated color information and the plural items of reference color information, specify one item of the reference color information which has the smallest error as reference color information that is most similar to the generated color information, and specify the identifying information that is related to the specified reference color information.

According to the present exemplary embodiment, therefore, the colors of many reaction surfaces can be identified with a relatively small amount of data.

The arithmetic unit should preferably calculate average values of the signal intensities of the respective R, G, B signals for all the pixels from the RGB bitmap image data generated by the image capturing unit, and generate color information represented by the differences between one and other two of the average values of the signal intensities of the respective R, G, B signals.

According to the present exemplary embodiment, characteristic variations of the individual image capturing elements of the image capturing unit, for example, can be averaged. Consequently, the color of the reaction surface can be identified with high accuracy.

The reference data storage should preferably store, in advance, color information generated by the arithmetic unit from the RGB bitmap data generated when the image capturing unit has captured images of the reaction surface that has caused a color reaction with gases, as reference color information.

According to the present exemplary embodiment, the plural items of reference color information stored in the reference data storage are dependent on the characteristics of the image capturing unit, making it easy to match the plural items of reference color information stored in the reference data storage and the image capturing characteristics of the image capturing unit.

The identifying information should preferably comprise information for identifying a reaction surface by a gas which has chemically reacted on the reaction surface.

According to the present exemplary embodiment, it is thus possible to output identifying information for identifying a gas which has chemically reacted with a reaction surface. Therefore, it is easy to specify the gas which has chemically reacted with the reaction surface.

An exemplary advantage according to the present invention is that the color of a reaction surface can be identified with a relatively small amount of data.

While an exemplary embodiment of the present invention has been described using specific terms, such description is for illustrative purposes only, and it is to be understood that changes and variations may be made without departing from the spirit or scope of the following claims.

What is claimed is:

1. A color identifying apparatus for identifying a color of a reaction surface which has caused a color reaction with a gas to be specified, comprising:
    a reference data storage that stores a plurality of associated sets of reference color information represented by a difference between one and the other remaining two of signal intensities of R, G, B signals of RGB bitmap images of a reaction surface which has caused a color reaction with a gas, and identifying information for identifying the reaction surface;
    an image capturing unit that captures an image of the reaction surface and generates RGB bitmap images of the reaction surface;
    an arithmetic unit that generates color information represented by the difference between one and the remaining other two signal intensities of R, G, B signals from the RGB bitmap images generated by said image capturing unit, checks the generated color information against the reference color information stored in said reference data storage, specifies the reference color information which corresponds to the generated color information, and specifies the identifying information which is related to the specified reference color information; and
    an output unit that outputs the identifying information specified by said arithmetic unit, and
    wherein said arithmetic unit calculates average values of the signal intensities of the respective R, G, B signals for all pixels from the RGB bitmap images generated by said image capturing unit, and generates color information represented by the differences between one and the remaining other two of the average values of the signal intensities of the respective R, G, B signals.

2. The color identifying apparatus according to claim 1, wherein said reference data storage stores, in advance, color information generated by said arithmetic unit from RGB bitmap images generated when said image capturing unit has captured images of a reaction surface that has caused a color reaction with gases, as said reference color information.

3. The color identifying apparatus according to claim 1, wherein said identifying information comprises information For identifying said reaction surface by the gas which has chemically reacted on said reaction surface.

4. A color identifying method adapted to be carried out by a color identifying apparatus including a reference data storage, comprising:
    storing, in said reference data storage, a plurality of associated sets of reference color information represented by a difference between one and the remaining other two of signal intensities of R, G, B signals of RGB bitmap images of a reaction surface which has caused a color reaction with a gas, and identifying information for identifying the reaction surface;
    capturing an image of the reaction surface and generating RGB bitmap images of the reaction surface;
    generating color information represented by the difference between one and the remaining other two signal intensities of R, G, B signals from the generated RGB bitmap images;
    specifying the reference color information which corresponds to the generated color information by checking the generated color information against the reference color information stored in said reference data storage;
    specifying the identifying information which is related to the specified reference color information; and
    outputting the specified identifying information,
    wherein said generating color information comprises calculating average values of the signal intensities of the respective R, G, B signals for all pixels from the generated RGB bitmap images, and generating color information represented by the differences between one and other two of the average values of the signal intensities of the respective R, G, B signals.

5. The color identifying method according to claim 4, wherein said storing comprises storing, in advance, color information generated by said color identifying apparatus, as said reference color information.

6. The color identifying method according to claim 4, wherein said identifying information comprises information for identifying said reaction surface by the gas which has chemically reacted on said reaction surface.

* * * * *